(12) United States Patent
Rault et al.

(10) Patent No.: US 6,696,085 B2
(45) Date of Patent: *Feb. 24, 2004

(54) USE OF AN ACRYLIC TYPE POLYMER AS DISINTEGRATING AGENT

(75) Inventors: Isabelle Rault, Mulhouse (FR); Etienne Pionnier, Mulhouse (FR)

(73) Assignee: Antares Pharma IPL AG, Zug (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/353,646

(22) Filed: Jul. 15, 1999

(65) Prior Publication Data

US 2002/0168404 A1 Nov. 14, 2002

(30) Foreign Application Priority Data

Jul. 20, 1998 (FR) .............................. 98 09221

(51) Int. Cl.[7] .................................. A61K 9/20
(52) U.S. Cl. ..................... 424/464; 424/468; 424/465; 424/474; 424/478; 424/466; 424/472; 424/475; 424/487
(58) Field of Search ................ 424/464, 465, 424/468, 474, 487, 466, 472, 475

(56) References Cited

U.S. PATENT DOCUMENTS

| 5,213,794 A | * | 5/1993 | Fritsch et al. ............. 424/78.01 |
| 5,409,711 A | * | 4/1995 | Mapelli et al. ............. 424/490 |
| 6,074,669 A | * | 6/2000 | Nagaprasad et al. ........ 424/458 |

OTHER PUBLICATIONS

Remington the science and practice of phramacy 19th edition, 1995, pp. 1639–1640.*
Webster II University Dictionary, 1994, p. 730.*

Ofoefule, "Effect of Polyethylene Glycol 4000 (PEG 4000) Solution on the In Vitro Release Profile of Nifedipine from Polymer Matrixes", Biol. Pharm. Bull. (1997), 20(5), pp. 574–576.

Kristoffersson et al., "Theophylline Tablet Formulations, Importance of the Composition of Tablets, the Compression Force used in Tableting and the In Vitro Stirring Speed on the Release of Theophylline from Two Layer Tablets" 1978.

Kala et al., "Granule Process Pharmaceutical Swelling Polymer Bind Contain Oxygen Function", Derwent database, Aug. 13, 1980.

Lehmann, "Formulation of Controlled Release Tablets with Acrylic Resins", Acta Pharm. Fenn, 93(2), pp. 55–74, (1984).

McGinity et al., "Controlled–Release Theophylline Tablet Formulations Containing Acrylic Resins. I. Dissolution Properties of Tablets", Drug Dev. Ind. Pharm. (1983), 9(1–2), pp. 57–68.

Cameron et al., "Controlled–Release Theophylline Tablet Formulations Containing Acrylic Resins, II. Combination Resin Formulations", Drug Dev. Ind. Pharm. (1987) 13(8), pp 1409–1427.

Gidwani et al., "Spray–Dried Enteric Solid Dispersion as a Novel Oral Delivery System for Pentapeptide Analog of Thymopentin", Drug Development and Industrial Pharmacy, 18(4), pp. 385–394, (1992).

Erdos, "Spontaneous Disintegration", Pharm. Ind. (1986) 48(5), pp. 503–507.

* cited by examiner

Primary Examiner—Russell Travers
Assistant Examiner—Shahnam Sharareh
(74) Attorney, Agent, or Firm—Winston & Strawn LLP

(57) ABSTRACT

The present invention provides for the use of a polymer of the acrylic type as a disintegration agent.

28 Claims, No Drawings

USE OF AN ACRYLIC TYPE POLYMER AS DISINTEGRATING AGENT

This is a continuation of a French Application 98 09221 filed on Jul. 20, 1998.

The present Application generally relates to the use of a polymer of acrylic type as a break-up or disintegration agent. It relates in particular to the use of a copolymer of acrylic type as disintegration agent or co-agent in a galenic form of tablet type, as well as a process for producing galenic forms of tablet type using such a copolymer as a disintegration agent or co-agent.

The agents most generally used for the production of galenic forms intended to disintegrate correspond to agents known as distintegration agents of the sodium carboxymethyl cellulose type, or to agents known as swelling agents of crospovidone or modified starch type.

While some of these agents allow tablets to be obtained which have a disintegration speed suited to the conditions in which they are used, while presenting acceptable pharmacotechnical characteristics (in particular hardness, friability and stability), this involves long and complex processes. In fact, the use of these agents as disintegration agents requires for example the creation of specific sub-structures such as microparticles or microgranules before the tablet is turned into its final galenic form, or the use of effervescent type reactions, which reactions themselves require the tablets to be manufactured in a low humidity medium.

SUMMARY OF INVENTION

The invention which is a subject of the present Application proposes a new use of a polymer of acrylic type and a new process which aims to remedy the drawbacks involved in the techniques of the prior art. The new use and the new process according to the invention also shows particularly appreciable performances for obtaining tablets which display appropriate disintegration properties under conditions of use or equivalent to this use while displaying very good pharmacotechnical characteristics (in particular hardness, friability, stability) before use and in particular during storage.

The polymers of acrylic type are, for their part, generally used in the prior art for the manufacture of sustained release tablets and/or for the production of enteric coatings. Among the different polymers of acrylic type known to a person skilled in the art, the US Pharmacopea National Formulary (USP/NF) makes a distinction in particular between methacrylic acid copolymers of type A, B or C and ammonium methacrylate copolymers of type A or B. It is in particular known that methacrylic acid copolymers of type A or B and ammonium methacrylate copolymers of type A or B can be used in the production of delay matrices (pH-dependent in the case of the first copolymers; pH-independent in the case of the second). The methacrylic acid copolymers of type C are for their part known as being able to be used in the production of different coatings: enteric coatings due to their gastro-resistent properties and their solubility in an intestinal medium at pH 5.5–7.5; insulation coatings intended to protect active ingredients in a tropical type environment; or also coatings intended to mask taste or smell.

DETAILED DESCRIPTION OF THE PREFFERED EMBODIEMENTS

The inventors have demonstrated that certain polymers of acrylic type, namely the methacrylic acid copolymers of type C according to the USP/NF, are, unexpectedly, capable of very significantly improving the disintegration speed of a tablet, while allowing a tablet to be obtained which has very good pharmacotechnical characteristics, and in particular very good cohesion. The use of a methacrylic acid copolymer of type C according to the invention has the particular advantage of allowing rapid disintegration tablets to be obtained, and in particular immediate type disintegration, which display, before use, very good pharmacotechnical characteristics (in particular, very good hardness and friability characteristics).

These very good pharmacotechnical characteristics simplify the packaging and storage of the tablets produced in this way: the tablets produced by means of the use or the process according to the invention do not require packaging specifically adapted to the protection of the structure of these tablets such as packaging with a peel-off film so as to avoid the extraction of the tablet from its cell by pushing with a finger.

These very good pharmacotechnical characteristics are also at the origin of the very good storage characteristics of said tablets over time (stability). These specific polymers of acrylic type according to the invention, in addition to the surprising disintegration effectiveness they offer, also have the notable advantage of being easy to use for producing tablets. In fact, they do not of themselves require the implementation of specific technologies to produce cohesive rapid disintegration tablets: any technology known to a person skilled in the art can be used, providing the other elements of the galenic form are chosen in such a manner as to allow this. In particular, they allow the production of cohesive rapid disintegration tablets by simple direct compression, without requiring the implementation of exacting technologies such as wet granulation.

A subject of the present Application is therefore, in general, the use of at least one methacrylic acid copolymer of type C according to the USP/NF as an agent or co-agent allowing the improvement of the disintegration speed of a tablet while allowing a tablet with a good cohesion to be obtained, in particular by simple direct compression. It relates in particular to the use of at least one methacrylic acid copolymer of type C according to the USP/NF as an agent or co-agent allowing or participating in the disintegration of a tablet, as well as a production process for tablets involving the use of at least one copolymer as a disintegration agent or co-agent in a tablet.

It relates in particular to the use of at least one methacrylic acid copolymer of type C according to the USP/NF as an agent or co-agent allowing or participating in rapid disintegration of immediate type of a tablet as well as a production process for rapid disintegration tablets, and in particular immediate disintegration tablets, using such a copolymer as a disintegration agent or co-agent.

The tablet disintegration effect observed according to the invention does not correspond to a simple erosion of mechanical type, but rather to an effect of the swelling type after appropriate hydration of the tablet.

By "tablet disintegration agent" is understood in the present Application an agent allowing an improvement in the disintegration speed observed for this tablet in the absence of this agent.

This improvement in tablet disintegration speed can naturally be optimized by choosing the other tablet characteristics (such as type and quantity of the tablet's components, mass, format, hardness of the tablet) such that they do not oppose or even that they enhance the disintegration phenomenon.

By "rapid tablet disintegration agent" is thus understood in the present Application an agent offering a significant improvement in the tablet's disintegration speed, as indicated above. The term "significant" can be appreciated using any statistical tool known to a person skilled in the art. Appropriate conditions for observing this significant improvement include those which consist in placing said tablet in medium conditions and in particular in composition, pH and temperature conditions suited to the disintegration of the tablet in question.

By "immediate type tablet disintegration agent" is understood an agent allowing the disintegration of said tablet over a period lasting approximately 25 seconds or less, preferably approximately 20 seconds or less, even more preferably approximately 10 seconds or less, when the tablet is tested under conditions appropriate for its disintegration, and when the other components of the tablet and its structure (mass, format, hardness) are chosen in such a way that they do not oppose, or they even enhance, the disintegration phenomenon. Appropriate conditions for testing the disintegration of a tablet include conditions which mimic those under under which said tablet is intended to break up. For example, in the case of a tablet intended to break up under the physiological conditions of a buccal cavity, such appropriate conditions include the fact of testing said tablet on an apparatus of Erweka ZT3® type in a saliva medium at 33° C. and pH 6.0.

The term "agent" used in the present Application also covers a co-agent situation. Thus the use according to the invention advantageously includes the use of a methacrylic acid copolymer of type C according to the USP/NF as an immediate type disintegration agent according to the invention, combined with the use of one or more known disintegration agents such as crospovidone (for example, that marketed under the trade mark Kollidon-CL® by BASF Aktiengesellschaft, Ludwigshafen, Germany).

The methacrylic acid copolymer(s) of type C used as disintegration agent(s) or co-agent(s) according to the invention can in particular be used for the production of any tablet requiring an improvement in the disintegration speed, and in particular a high disintegration speed. This is in particular the case for tablets adapted or intended for a pharmaceutical, veterinary or hygiene use. There can in particular be mentioned pharmaceutical, veterinary or hygiene tablets intended for administration by oral route for disintegration in the buccal cavity, those intended for administration by oral route for deferred disintegration, for example deferred to the level of the intestines, or also those intended for administration by vaginal route.

The present Application relates in particular to the use of a methacrylic acid copolymer of type C according to the USP/NF in a tablet intended to break up rapidly (of immediate type) in the buccal cavity. Such a copolymer thus used or implemented or as a disintegration agent (or co-agent) in fact allows tablets to be obtained which are capable (after hydration with saliva) of breaking up in the buccal cavity over a very short period of time (in a particularly preferential manner, periods of less than 10 seconds are obtained). The suspension created in this way benefits from a large exchange surface, and the active ingredients are released in a particularly rapid manner. Apart from the usefulness of this galenic form in terms of bioavailability, it has other advantages, one of the main advantages undoubtedly being its ease of use. In fact, the patient needs no water in order to follow his treatment, resulting in better observance. For young children or the elderly, this form also requires no chewing or deglutition effort.

The buccal disintegration tablets can however have the drawback of an unpleasant taste and/or smell. In order to reduce or even eliminate the unpleasant smell and/or taste of the galenic form, sweeteners and/or flavourings can be added to the formulation, and/or those components which have an unpleasant taste and/or smell can be coated (for example, the active ingredient can be coated). Remarkably, such components modified by coating can be included in the use according to the invention without significantly modifying its disintegration speed.

The proportions in which said (or each of said) methacrylic acid copolymer(s) of type C must be used according to the invention can easily be tested by trial and error using techniques known to a person skilled in the art, according to the complete formulation of the tablet chosen, and according to the effect sought. For information, these proportions are generally comprised between approximately 5 and 50% of the total mass of the tablet.

The methacrylic acid copolymer(s) of type C implemented, or used as disintegration agent(s) or co-agent(s) according to the invention do not cause any restriction in the possible nature of the other elements of the galenic form. It or they can thus be combined with any substance or excipient appropriate to the type of appliation for which the tablet is intended.

According to a provision of the invention, said use turns to good account the fact that the methacrylic acid copolymers of type C are both gastro-resistant and soluble in an intestinal medium in order to combine them with one or more copolymer(s) of ammonium methacrylate of type A and/or B according to the USP/NF (delay matrix independent of the pH), in order to encourage the release of the active ingredient in the intestine. The process and the use according to the invention then allow a tablet to be obtained intended for administration by oral route, which does not break up at the level of the intestines, in very short periods of time, or even over an immediate type of time period if necessary.

For an application by vaginal route, the use according to the invention can further comprise the implementation of a bioadhesive compound.

In a quite general manner, the use of at least one methacrylic acid copolymer of type C according to the invention further comprises the use of an active ingredient or a placebo, the use of a diluent (such as dextrose), of a hardness enhancing agent (such as sorbitol), of a lubricant (such as magnesium stearate or groundnut oil), and optionally a binding agent (such as maize starch).

More particularly, the use according to the invention can also further comprise the use of excipients or substances among those playing the following roles:

disintegration or disintegration agents such as for example crospovidone (marketed under the trademark Kollidon-CL® for example), sodium croscarmellose, sodium carboxymethyl starch, partially substituted hydroxypropylcellulose, sodium starch glycolate, in a proportion which can vary from 1% to 50%, soluble or slightly soluble swelling agents, diluents such as lactose, binding agents such as maize starch, lubricants such as magnesium stearate, flow agents such as colloidal silica, solubilization agents, flavourings, sweeteners, plastifiers, antioxidants, film forming and coating agents, agents involved in the composition of the polishing and shining solution, agents providing thermal protection of the active ingredient such as saccharose derivatives, excipients or substances providing bioadhesion such as acrylic acid derivatives, the copolymer of methylvinylether and maleic anhydride, guar gum, xanthane gum, carouba, carraghenates, pectin, a biological or synthetic protein alone or in combination with other proteins of biological or synthetic origin, cyclodextrins, hydroxypropylbetacyclodextrins, betacyclodextrins and their derivatives.

The use according to the invention allows any desired active ingredient to be combined with the tablet. There can in particular be mentioned antihistamines, anticholergenics, mineral elements, allergens, surface, local or general anesthetics, antipyretics, non-opiate analgesics, opiate analgesics, anticholinergic and non-anticholinergic antispasmodics, non-steroid anti-inflammatories such as tiaprofenic acid, indomethacin, diclofenac, ibuprofen, ketoprofen, naproxen, piroxicam, steroid anti-inflammatories such as betamethasone, prednisolone, cytotoxics, antihormonal agents, antianaemics, antiemetics, antiasthenics, antihypertensives including beta-blockers such as propranolol, atenolol, metoprolol, conversion enzyme inhibitors such as captopril, enalapril, angiotensin II antagonists, calcium inhibitors such as nifedipine and diltiazem, central action antihypertensives, vasodilators, hypolipemiants, oral antidiabetics, anticoagulants, platelet antiaggregants, calcium inhibitors, nitrated derivatives used in the treatment of coronary insufficiency, non-nitrated antianginals, diuretics, digitalin derivatives and related derivatives, antiarhythmics, antihypotensives and circulatory analeptics, vasodilators, anti-ischemics, vasculoprotectors and venotonics, hormones, antiherpetics, antiphotosensitizers, antiulceratives such as ranitidine, cimetidine, antacids, laxatives, antidiarrheals, antifungals, cholelitholytics, interferons, enzymes, antispasmodics, antibacterials, antiseptics, antiherpetics, uterorelaxants, oxytocics, oestrogens, progestatives, oestroprogestatives, the active ingredients indicated in lactation such as bromocriptine, the active ingredients indicated in the treatment of sterility, antigonadotropics, anticoagulants, thrombolytics, antifibrinolytics, vitamins, haemostatics, cyclosporines, alkylating agents, antibiotics, antivirals, antiparasitics, vaccines, diagnostic products, the active ingredients indicated in the treatment of obesity, orexigenics, the active ingredients indicated in the treatment of the correction of metabolic abnormalities, the active ingredients indicated in oral and enteral nutrition, anticonvulsives, antiparkinsonians, antimyasthenics, the active ingredients indicated in the treatment of Alzheimer's disease, antimigraine agents, neuroleptics, anxiolytics, hypnotics, sedatives, antidepressants, normothymrics, psychostimulants, the active ingredients indicated in the treatment of states of alcohol addiction, tobacco disintoxication, opiate disintoxication, antiglaucoma agents, mydriatics, bronchodilators, antiasthmatics, antitussives, bronchial fluidifiers, (topical) revulsives, the active ingredients indicated in the treatment of osteopathies, the active ingredients indicated in the treatment of acute attacks of gout, the active ingredients indicated in the treatment of hypouricemia, the active ingredients indicated in the treatment of algodystrophiae, myorelaxants, the active ingredients indicated in the treatment of arthrosis, correctors of hyposialoses, the active ingredients indicated in the treatment of urinary lithiasis, the active ingredients indicated in the treatment of renal insufficiency, the active ingredients indicated in the treatment of enuresis, the active ingredients indicated in the treatment of retrograde ejaculation, the active ingredients indicated in the treatment of impotence.

The methacrylic acid copolymer(s) of type C according to the USP/NF used as a disintegration agent according to the invention can be incorporated by mixture into the tablet mass, or can only be part of certain sub-structures of the tablet, for example be incorporated with micro- or nano-particles (or micro- or nano-capsules) included in a tablet, and/or be incorporated into a layer of a multi-layer tablet, in particular in a layer intended for rapid disintegration. This tablet, intended for rapid disintegration, whether mono-layered, particular, multi-layered or a combination of these arrangements, is advantageously presented in the form of a bioadhesive tablet (for example, for rapid disintegration by vaginal route), and/or a tablet for the rapid but deferred release of the active ingredient(s) (for example, rapid disintegration at the level of the intestines after administration by oral route), or a tablet for the rapid and immediate release of the active ingredient(s) (for example, rapid disintegration in the mouth).

The at least one methacrylic acid copolymer of type C and the other disintegration agent(s) are present in a weight ratio of about 1:10 to about 1:1 to about 50:1. It is advantageous that the at least one methacrylic acid copolymer of type C be present in an amount that is at least about the same (i.e. 50:50) or that is greater than that of the other disintegration agents, with a ratio of 2:1 being preferred as shown in the examples.

Advantageously, the use according to the invention comprises a use of said tablet mass, or, where appropriate, of said tablet sub-structure in an essentially pulverulent form before being turned into a galenic form.

The use of a methacrylic acid copolymer of type C as a disintegration agent of a tablet according to the invention allows said tablet to be obtained (or, where appropriate, allows said tablet sub-structure to be obtained in which said copolymer is incorporated) using any technique known to a person skilled in the art, such as wet granulation, dry granulation and compacting, extrusion, as well as, advantageously, such as direct compression. Restriction to one or more types of technique can be observed according to the nature and/or proportion of the other components used in the production of said tablet, and/or according to the structure to be given to this tablet. Such a restriction is however not a result of said methacrylic acid copolymer of type C used. Preferentially, the use according to the invention comprises turning said tablet, or, where appropriate, said tablet sub-structure into galenic form, by simple direct compression.

Remarkably, the use according to the invention allows tablets to be obtained which have very good pharmacotechnical characteristics and which in particular, after being turned into a galenic form, display a hardness comprised between approximately 0.2 and 10 Kp and a friability comprised between approximately 0 and 25%.

The use according to the invention is suited to the production of tablets of any mass and any format, without limitation. Typically, for medical, veterinary or hygiene uses, tablet masses ranging from 50 to 200 mg are produced and formats of D6R4, flat D6, D7R5, D9R7, flat D9, flat D10 type are used.

Particularly remarkably, the use according to the invention allows tablets to be obtained which, while having very good pharmacotechnical characteristics, are capable of breaking up in a time period of less than approximately 25 seconds, preferably in a time period less than or equal to approximately 20 seconds, even more preferably less than or equal to approximately 10 seconds, when they are placed in appropriate conditions for their disintegration. The determination of appropriate conditions is known to a person skilled in the art, and examples of this are given in the present Application.

Examples of methacrylic acid copolymers of type C according to the USP/NF which can be used according to the invention include those marketed by the company Röhm GmbH (Darmstadt, Germany), under the name Eudragit L100-55® (pulverulent form), or Eudragit L30D-55® (aqueous dispersion). Eudragit L100-55® corresponds to the following formula:

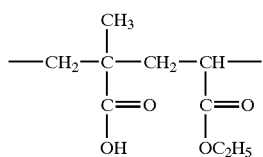

A subject of the present invention is also production process for tablets, in particular rapid disintegration tablets, and in particular immediate type rapid disintegration tablets, said process involving the use of at least one methacrylic acid copolymer of type C according to the USP/NF as a disintegration agent or co-agent, and in particular involving the use of at least one methacrylic acid copolymer of type C as used according to the invention. Preferentially and advantageously, the process according to the invention further comprises turning the tablets into galenic form by simple direct compression.

The following examples are given for illustration purposes, but do not in any way limit the invention which is the subject of the present Application.

In these examples, different pharmacotechnical parameters are measured using standard techniques. Among these parameters there can in particular be mentioned hardness, friability as well as stability of the tablet obtained according to the use and/or the process of the invention.

Among the means available to a person skilled in the art for measuring such parameters, there can be mentioned:

a Schleuninger 2E/205 type apparatus for measuring hardness, a drum friability meter of ribbed drum type (Roche) for measuring the friability, a suitable friability measurement protocol which includes placing a representative sample of tablets (for example, 10 tablets) in a drum rotating clockwise at 25 rpm for 10 minutes, measuring the average mass of a tablet before treatment ($m_{t0}$), and after removing the dust at the end of this treatment ($m_{10min}$), and calculating the friability % as follows:

$$\text{friability \%} = \frac{m_{t10\ min}}{(m_{t0} - m_{t10\ min})} \times 100$$

a tablet disintegration apparatus of Erweka ZT3 type using a suitable measurement protocol which includes placing 1 tablet in each of 6 glass tubes in a basket, then adding the disk. The basket is then suspended and maintained above the beaker filled with saliva medium. The disintegration time is measured from the time the basket is lowered into the beaker until total disintegration of the tablets. Composition of the saliva medium used (pH=6): KCl: 1.20 g/l; $MgCl_2$, $6H_2O$: 0.05 g/l; $CaCl_2$, $6H_2O$: 0.15 g/l; KSCN: 0.10 g/l.

climatic chambers for measuring stability, a suitable measurement protocol which includes monitoring pharmacotechnical parameters such as hardness and friability over time (for example every three months) in a representative sample of tablets placed under different climatic conditions (for example at 25° C. and at 45° C.), and/or monitoring the stability of a compound (for example an active ingredient) initially included in such tablets.

EXAMPLE 1

Tablets are produced by direct compression, following the "Eudragit" formula indicated in Table 1 below. Tablets corresponding to the control formula are produced under equivalent conditions. These formulae are chosen in an appropriate manner in order to allow rapid disintegration in the buccal cavity, after they have been turned into a galenic form and when they are used.

The tablets are of a flat, chamfered shape and a diameter equal to 8 mm. They are completed to 205 mg each.

TABLE 1

| Excipients | Eudragit formula (% by mass) | Control formula (% by mass) |
|---|---|---|
| Eudragit L100-55 ® (Rhöm, SPCI) | 30.00 | — |
| Kollidon-CL ® (BASF) | 15.00 | 15.00 |
| Dextrose (Roquette) | 51.70 | 81.70 |
| Synthetic vanilla (SBI) | 3.00 | 3.00 |
| Groundnut oil | 0.30 | 0.30 |

The pharmacotechnical parameters, and in particular the average hardness and the average disintegration time for these two groups of tablets are then measured. The results obtained are illustrated by Table 2 below.

TABLE 2

| Formula | Hardness (Kp) | Disintegration time in seconds (*) |
|---|---|---|
| Eudragit formula | 1.6–2.2 | 7–13 |
| Control formula | 1.2–1.5 | 20–25 |
| | 3.5 | 25–30 |

(*) disintegration time tested on an Erweka ZT3 apparatus in a saliva medium at 33° C. and at pH 6.0.

The pharmacotechnical results indicate that the Eudragit L100-5®, which is a methacrylic acid copolymer of type C according to the USP/NF, significantly improves a tablet's disintegration time, in order to reach approximately immediate disintegration times (less than 20 seconds). The use of Eudragit L100-55® allowed the tablet's disintegration time to be reduced by approximately 50% on average, while obtaining tablets with good cohesion. The friability of the "Eudragit" formula tablets is 8.8%.

EXAMPLE 2

It is also possible to use the following "Eudragit" formula (cf. the table below) in order to obtain, by direct compression, placebo tablets with a disintegration time of 7 seconds (n=6), as measured in a saliva medium at 33° C. and pH 6.0 on an Erweka ZT3 apparatus. In this case, the groundnut oil was replaced with magnesium stearate and sorbitol was added. These two agents respectively improve the flow and compressibility of the mixture of powders. It is possible to work with lower hardnesses while obtaining a tablet which is not very friable.

Tablets are produced by direct compression on a compressing machine of alternative Korsch EKO type. 1.1 kg of the final powder mixture is used, i.e. 10,000 tablets completed to 110 mg. 330 g of Eudragit L100-55®; 165 g of Kollidon-CL®. 535.7 g of dextrose; 33 g of sorbitol and 33 g of synthetic vanilla (Givaudan-Roure) are weighed.

The mixture is mixed with a 'TURBULA' for 5 minutes; 3.3 g of magnesium stearate (magnesic) is added to the mixture obtained. Mixing with a 'TURBULA' is carried out for 30 seconds; the mixture is compressed; the format of the tablets is D7R5 (diameter 7 mm and radius 5 mm) with a thickness of 4 mm.

As illustrated below, the tablets obtained have a hardness of 0.4 Kp, a friability of 2.7% and a disintegration time in a saliva medium (Erweka ZT3 apparatus) at 33° C. and pH 6.0 of 7 seconds.

TABLE 3

| Excipients | Eudragit formula (% by mass) | Control formula (% by mass) |
| --- | --- | --- |
| Eudragit L100-55 ® (Rhom, SPCI) | 30.00 | — |
| Kollidon CL ® (BASF) | 15.00 | 15.00 |
| Dextrose (Roferose G) (Roquette) | 48.75 | 78.75 |
| Sorbitol P100T (Roquette) | 3.00 | 3.00 |
| Synthetic vanilla (SBI) | 3.00 | 3.00 |
| Magnesium stearate | 0.25 | 0.25 |

The pharmacotechnical parameters of the tablets are measured using standard techniques.

The hardness and disintegration time results for these tablets are set out in Table 4 below.

TABLE 4

| Formula | Hardness (Kp) | Disintegration time in seconds (*) | Friability in % |
| --- | --- | --- | --- |
| Eudragit formula | 0.4 | 7 | 2.7 |
| Control formula | 1.1 | 13 | 0.3 |

(*) disintegration time tested on an Erweka ZT3 apparatus in a saliva medium at 33° C. and at pH 6.0.

Use of Eudragit L100-55 allowed the disintegration time to be reduced by almost half. However, it appears quite clear that Eudragit also facilitates compressibility as it is impossible to work the control formula with low compression forces (tablet hardness lower than 1 Kp). The latter formula cannot be the subject of an industrial development as it does not fulfill the necessary galenic characteristics.

EXAMPLE 3

The formula used in Example 2 is produced in such a manner as to obtain 200 mg tablets. The tablet format is D9R7 (diameter 9 mm and radius of curvature 7 mm), with a thickness of 5 mm.

The pharmacotechnical parameters of the tablets are measured using standard techniques.

The hardness and disintegration time results for these tablets are set out in Table 5 below.

TABLE 5

| Formula | Hardness (Kp) | Disintegration time (seconds) | Friability in % |
| --- | --- | --- | --- |
| Eudragit formula | 2.8 | 16 | 0.9 |
| Control formula | 2.4 | 23 | 0.5 |

In this instance, the control formula cannot be compressed to a hardness of less than 2 Kp; the tablets produced with the Eudragit formula were therefore produced to a comparable hardness. Thanks to the use of the Eudragit, a reduction in disintegration time is obtained of the order of 30%.

EXAMPLE 4

The use of a methacrylic acid copolymer of type C (USP/NF) as a disintegration agent or co-agent according to the invention allows the disintegration speed of tablets to be modulated. This modulation can in particular be carried out by adjusting the quantity of methacrylic acid copolymer of type C added.

There follows a presentation of an example of modulation according to the invention on tablets loaded with Loperamide as active ingredient.

Tablets are produced following the "Eudragit" formula indicated in Table 5 above, by mixing the different powders of the formula, then turning into a galenic form by direct compression. Control tablets without a methacrylic acid copolymer of type C (Eudragit L100-55®) are produced under the same conditions. The tablets of both formulae are presented in a D7R5 type format. They are all completed to 110 mg.

TABLE 6

| Excipients | Eudragit formula (in %) | Control formula (in %) |
| --- | --- | --- |
| Loperamide HCl (francochim) | 2.00 | 2.00 |
| Eudragit L100-55 (Rhom, SPCI) | 30.00 | — |
| Kollidon Cl (BASF) | 15.00 | 15.00 |
| Dextrose (Roferose G) Roquette | 49.7 | 79.7 |
| Sorbitol P100T (Roquette) | 3.00 | 3.00 |
| Magnesium stearate (Lambert Rivière) | 0.30 | 0.25 |

Pharmaceutical Technology Parameters:

TABLE 7

| Formula | Hardness (Kp) | Disintegration time in seconds* | Friability in % |
| --- | --- | --- | --- |
| Eudragit formula | 1.5 ± 0.4 | 9 | 1.17 |
| Control formula | 1.41 ± 0.8 | 13 | 0.55 |

*disintegration time tested on an Erweka ZT3 apparatus at pH 6.0

The use of Eudragit L100-55 in a proportion of 30% in the formula reduces by 30% the disintegration time of the tablet studied. Similarly, it should be noted that the control formulation is not satisfactory from a galenic point of view. In fact, when sufficient compression force is applied to obtain a tablet with a hardness less than or equal to 1.5 Kp, the tablet cleaves and sticks to the dies. The test results shown in Table 7 originate from tablets produced at a very slow rate and sorted. It is clear that this formulation without Eudragit cannot be produced on an industrial basis.

COMPARATIVE EXAMPLE 5

Methacrylic acid copolymers of type A or B according to the USP/NF were tested for any rapid disintegration agent properties with respect to the tablets, under conditions comparable to those observed in tablets comprising a methacrylic acid copolymer of type C shown in Examples 1 or 2 above.

Tests A, B, C and D were carried out according to the following protocol summarized in Table 8. The tablets are in flat D9 format.

TABLE 8

|  | Test A (% by mass) | Test B (% by mass) | Test C (% by mass) | Test D (% by mass) |
| --- | --- | --- | --- | --- |
| Eudragit L100-55 (Rhom Pharma) | 30.00 | | | |
| Eudragit L100 (Rhom Pharma) | | | 30.00 | |
| Eudragit S100 (Rhom Pharma) | | | | 30.00 |
| Kollidon CL (BASF) | 15.00 | 15.00 | 15.00 | 15.00 |
| Dextrose (Roferose G) (Roquette) | 48.75 | 78.75 | 48.75 | 48.75 |
| Sorbitol P100T (Roquette) | 3.00 | 3.00 | 3.00 | 3.00 |
| Synthetic vanilla (SBI) | 3.00 | 3.00 | 3.00 | 3.00 |
| Groundnut oil | 0.25 | 0.25 | 0.25 | 0.25 |
| Final mass (mg) | 210 | 218 | 218 | 218 |

Test A carried out with Eudragit L100-55 allows tablets to be obtained with a hardness of 1.4 Kp, a disintegration time of 10 seconds and a friability of 7.4%.

In test B which corresponds to the control test, the tablets prepared in such a way as to obtain a hardness of approximately 1.5 Kp have disintegration times of between 20 and 25 seconds.

The tests C were therefore carried out with Eudragit L100® as disintegration agent (methacrylic acid copolymer of type A according to the USP/NF). 218 mg tablets were produced by direct compression. In order to limit the disintegration time, the tablets were produced with the lowest hardness possible. Given the poor compressibility of the mixture of powders, the minimum acceptable hardness is in the region of 3 Kp (precisely 3.24 Kp). Under these conditions, the disintegration time obtained is 29.8 seconds, and measurement of friability proves impossible: the tablet cleaves. At best, such tablets therefore display medium disintegration characteristics (without reaching immediate type disintegration), and deficient pharmacotechnical characteristics. With a methacrylic acid copolymer of type A, a pulverulent mixture is also obtained which does not show itself to be suitable for compression, whether at laboratory or industry rates.

Use of a methacrylic acid copolymer of type A according to the USP/NF as a disintegration agent does not therefore allow tablets to be obtained which display disintegration and pharmacotechnical characteristics (in particular hardness and friability) comparable with those observed using a methacrylic acid copolymer of type C according to the invention.

The tests D were also carried out with Eudragit S100® as disintegration agent (methacrylic acid copolymer of type B according to the USP/NF). The tablets are completed to 218 mg, have a hardness of 2.9 Kp. An average disintegration time of 51.6 seconds was measured. The use of a methacrylic acid copolymer of type B USP/NF does not allow tablets to be obtained with an appropriate disintegration rate.

The comparison between the results obtained with the methacrylic acid copolymers of type A or B (illustrated above) or with the ammonium methacrylate copolymers of type A or B, and those obtained with methacrylic acid copolymers of type C (illustrated with Eudragit L100–55® in Examples 1 to 3 above in particular) demonstrates that, suprisingly, amongst these different acrylic type polymers, only the methacrylic acid copolymers of type C allow disintegration times to be obtained which are less than or equal to 25 seconds on average for a tablet having a maximum mass in the region of 200 mg, while endowing the tablets with good pharmacotechnical characteristics (in particular, hardness, friability and stability). Remarkably, times of less than 10 seconds were able to be recorded, while observing good pharmacotechnical characteristics. Eudragit L100-55® also offers the advantage of being a powder which displays a good compressibility, which allows a tablet to be obtained with a good cohesion while working with low compression forces. Its use is therefore advantageous at the industrial level.

What is claimed is:

1. A tablet that has disintegration properties when placed in a buccal or vaginal cavity of a subject, the tablet having a mass and comprising an active ingredient, a first disintegration agent of at least one Type C methacrylic acid copolymer according to the U.S. Pharmacopea National Formulary US/NF, and at least one second disintegration agent that is different from the first disintegration agent, with the first disintegration agent or agents being present in a total amount that provides a weight ratio of about 1:1 to about 50:1 with respect to the total amount of the second disintegration agent or agents, wherein the active ingredient and the first and second disintegration agents are incorporated into the mass of the tablet or into the mass of a sub-structure of the tablet so that the tablet has a hardness of between approximately 0.2 and 10 Kp and a friability of between approximately 0 and 25%, and the mass disintegrates in less than approximately 25 seconds when placed in the subject's buccal or vaginal cavity.

2. The tablet of claim 1, wherein the total amount of the second disintegration agent or agents in the tablet is 5 to 50% by mass with respect to the total mass of the tablet.

3. The tablet of claim 1, wherein the second disintegration agent comprises crospovidone, croscarmellose, carboxymethyl starch, hydroxypropyl cellulose, starch glycolate, a sodium salt thereof or mixtures thereof.

4. The tablet of claim 1, wherein the total amount of the second disintegration agent or agents in the tablet is 1 to 50% by mass with respect to the total mass of the tablet.

5. The tablet of claim 1, wherein the tablet has a hardness of above 0.5 Kp, a friability of between approximately 0.9 and 7.4%, and the mass disintegrates in less than approximately 20 seconds when placed in the subject's buccal or vaginal cavity.

6. The tablet of claim 1, wherein the mass disintegrates in less than approximately 10 seconds when placed in the subject's buccal or vaginal cavity.

7. The tablet of claim 1, wherein the tablet has a sub-structure selected from the group consisting of a tablet micro- or nano-particle, a tablet micro-or nano-capsule, and a tablet layer.

8. The tablet of claim 1, wherein the mass, active agent and other tablet ingredients axe directly compressed and the tablet is in a form for oral administration and disintegration in a buccal cavity.

9. The tablet of claim 1, which further comprises a bioadhesive compound so that the tablet can be adhered to the subject's vaginal cavity.

10. A process for preparing a tablet that has disintegration properties when placed in a buccal or vaginal cavity of a subject, the tablet having a mass and including an active ingredient, with the process comprising incorporating into the mass of the tablet or into the mass of a sub-structure of the tablet a first disintegration agent of at least one Type C methacrylic acid copolymer according to the U.S. Pharmacopea National Formulary US/NF, and at least one second disintegration agent that is different from the first disintegration agent, with the first disintegration agent or agents being present in a total amount that provides a weight ratio of about 1:1 to about 50:1 with respect to the total amount of the second disintegration agent or agents, so that the tablet has a hardness of between approximately 0.2 and 10 Kp and a friability of between approximately 0 and 25%, and the mass disintegrates in less than approximately 25 seconds when placed in the subject's buccal or vaginal cavity.

11. The process of claim 10, wherein the total amount of the second disintegration agent or agents in the tablet is 5 to 50% by mass with respect to the total mass of the tablet.

12. The process of claim 10, wherein the second disintegration agent comprises crospovidone, croscarmellose, carboxymethyl starch, hydroxypropyl cellulose, starch glycolate, or a sodium salt or mixture thereof.

13. The process of claim 10, wherein the total amount of the second disintegration agent or agents in the tablet is 1 to 50% by mass with respect to the total mass of the tablet.

14. The process of claim 10, wherein the tablet has a hardness of above 1.5 Kp, a friability of between approximately 0.9 and 7.4%, and the mass disintegrates in less than approximately 20 seconds when placed in the subject's buccal or vaginal cavity.

15. The process of claim 10, wherein the mass disintegrates in less than approximately 10 seconds when placed in the subject's buccal or vaginal cavity.

16. The process of claim 10, wherein the tablet has a substructure selected from the group consisting of a tablet micro- or nano-particle, a tablet micro-or nano-capsule, and a tablet layer.

17. The process of claim 10, wherein the tablet is obtained by directly compressing the mass, active agent and other tablet ingredients.

18. A tablet prepared by the process of claim 10, and in a form for oral administration and disintegration in a buccal cavity.

19. A tablet prepared by the process of claim 10, and which further comprises a bioadhesive compound so that the tablet can be adhered to the subject's vaginal cavity.

20. A method for releasing an active ingredient into a subject's buccal cavity which comprises:
preparing a tablet by the process of claim 10;
orally administering the tablet to the subject's buccal cavity where it can disintegrate to release the active ingredient.

21. The method of claim 20, wherein the tablet is obtained by directly compressing the mass, active agent and other tablet ingredients.

22. The method of claim 20, wherein the mass disintegrates in less than approximately 10 to 20 seconds alter placed in the subject's buccal cavity.

23. A method for releasing an active ingredient into a subject's buccal cavity which comprises orally administering the tablet of claim 1 to the subject's buccal cavity where it can disintegrate to release the active ingredient.

24. The method of claim 23 wherein the mass disintegrates in less than approximately 10 to 20 seconds after being placed in the subject's buccal cavity.

25. The tablet of claim 1, wherein the Type C methacrylic acid copolymer is a compound having the formula:

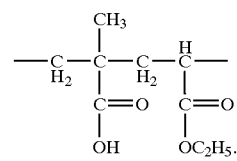

26. The tablet of claim 1, wherein the weight ratio of first and second disintegration agents is 1:1 to 2:1, the first disintegration agent is a compound having the formula:

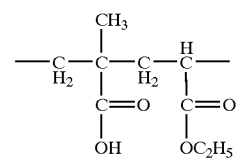

and the second disintegration agent includes crospovidone.

27. The process of claim 10, wherein the Type C methacrylic acid copolymer is a compound having the formula:

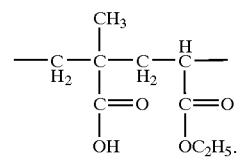

28. The process of claim 10, wherein the weight ratio of first and second disintegration agents is 1:1 to 2:1, the first disintegration agent is a compound having the formula:

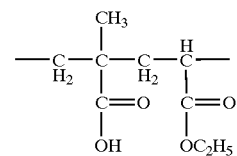

and the second disintegration agent includes crospovidone.

* * * * *

UNITED STATES PATENT AND TRADEMARK OFFICE
CERTIFICATE OF CORRECTION

PATENT NO. : 6,696,085 B2
DATED : February 24, 2004
INVENTOR(S) : Rault et al.

It is certified that error appears in the above-identified patent and that said Letters Patent is hereby corrected as shown below:

Title page,
Item [57], ABSTRACT, delete the text of the abstract and insert the following:
-- A tablet that has disintegration properties when placed in a buccal or vaginal cavity of a subject, the tablet having a mass and comprising an active ingredient, a first disintegration agent of at least one Type C methacrylic acid copolymer according to the U.S. Pharmacopoeia National Formulary US/NF, and at least one second disintegration agent that is different from the first disintegration agent, with the first disintegration agent or agents being present in a total amount that provides a weight ratio of about 1:1 to about 50:1 with respect to the total amount of the second disintegration agent or agents, wherein the active ingredient and the first and second disintegration agents are incorporated into the mass of the tablet or into the mass of a substructure of the tablet so that the tablet has a hardness of between approximately 0.2 and 10 Kp and a friability of between approximately 0 and 25%, and the mass disintegrates in less than approximately 25 seconds when placed in the subject's buccal or vaginal cavity. --.

Column 1,
Lines 4-5, delete "This is a continuation of a French Application 98 09221 filed on Jul. 20, 1998."

Column 12,
Line 53, change "of about 0.5 Kp," to -- of about 1.5 Kp, --.
Line 65, change "ingredients axe directly" to -- ingredients are directly --.

Column 14,
Line 2, change "10 to 20 seconds alter" to -- 10 to 20 seconds after --.

Signed and Sealed this

Twentieth Day of July, 2004

JON W. DUDAS
*Acting Director of the United States Patent and Trademark Office*